United States Patent [19]

Mazzara et al.

[11] Patent Number: 5,614,404
[45] Date of Patent: Mar. 25, 1997

[54] SELF-ASSEMBLED, DEFECTIVE, NON-SELF-PROPAGATING LENTIVIRUS PARTICLES

[75] Inventors: Gail P. Mazzara, Winchester; Bryan Roberts, Cambridge; Dennis L. Panicali, Acton, all of Mass.; Virginia Stallard, Seattle, Wash.; Linda R. Gritz, Sommerville; Anna Mahe, Natick, both of Mass.

[73] Assignee: Theriod Biologics, Incorporated, Cambridge, Mass.

[21] Appl. No.: 995,923

[22] Filed: Dec. 21, 1992

Related U.S. Application Data

[63] Continuation of Ser. No. 540,109, Jun. 19, 1990, abandoned, which is a continuation-in-part of Ser. No. 360,027, Jun. 1, 1989, abandoned, which is a continuation-in-part of Ser. No. 205,454, Jun. 10, 1988, abandoned.

[51] Int. Cl.$^6$ .......................... C12N 15/86; C12N 15/63; A61K 39/21; C07K 14/155
[52] U.S. Cl. ...................... 435/236; 435/69.1; 435/69.3; 435/172.3; 435/320.1; 930/221
[58] Field of Search .................. 435/236, 320.1, 435/69.1, 69.3, 172.3; 930/221

[56] References Cited

U.S. PATENT DOCUMENTS 4,603,112  7/1986  Paoletti et al. ...................... 435/235.1

FOREIGN PATENT DOCUMENTS

| 0302801 | 8/1987 | European Pat. Off. . |
|---|---|---|
| 243029 | 10/1987 | European Pat. Off. . |
| 245136 | 11/1987 | European Pat. Off. . |
| 0334301 | 9/1989 | European Pat. Off. . |
| 2181435 | 4/1987 | United Kingdom . |
| WO87/02038 | 4/1987 | WIPO . |
| WO87/06258 | 10/1987 | WIPO . |
| WO/88/02026 | 3/1988 | WIPO . |
| WO/88/03562 | 5/1988 | WIPO . |
| WO/88/03563 | 5/1988 | WIPO . |

OTHER PUBLICATIONS

R. Mann et al (1983) Cell 33:153–159.
A. Lever et al (1989) J. Virology 63(9):4085–4087.
Fields, B.N. et al, Eds. *Fundamental Virology*, 2nd Ed. New York: Raven Press, 1991, pp. 15, 92–93.
Haffar et al., J. Virol. 64(6):2653–2659 (1990).
S. Hu et al., *Nature*, 302:537–540 (1986).
S. Chakrabarti et al., *Nature*, 320:535–537 (1986).
M. P. Kieny et al., *Biotechnology*, 4:790–795 (1986).
J. M. Zarling et al., *Nature*, 323:344–346 (1986).
S. Hu et al., *Nature*, 328:721–723 (1987).
D. Zagury et al., *Nature*, 326:249–250 (1987).
D. Zagury et al., *Nature*, 332:728–731 (1988).
G. L. Smith et al., *Gene*, 25:21–28 (1983).
T. Shioda et al., *Virology* 175:139–148 (1990).
D. Panicali et al.,*Proc. Natl. Acad. Sci. USA*, 79:4927–4931 (1982).
D. Panicali et al., *Proc. Natl. Acad. Sci. USA*, 80:5364–5368 (1983).
O. Haffar et al., *J. Virol.* 64:2653–2659 (Jun. 1990).
V. Karacostas et al., *Proc. Natl. Acad. Sci. USA* 86:8964–8967 (Nov. 1989).
M. E. Perkus et al., *Science* 229:981–984 (1985).
M. Delchambre et al., *The EMBO J.* 8: 2653–2660 (1989).
M. L. Bosch et al., *Science* 244:694–697 (1989).
S. D. Gowda et al., *J. Biol. Chem.* 264: 8459–8460 (May 25, 1989). Abstract Provided Only.
G. Rautmann et al., *AIDS Res. Hum. Retroviruses* 5:147–157 (Apr. 1989). Abstract Provided Only.
S. D. Gowda et al., *J. Virol.* 63:1451–1454 (Mar. 1989). Abstract Provided Only.
S. A. Popov et al., *Mol. Gen. Mikrobiol. Virusol.* 9:36–39 (Sep. 1988). Abstract Provided Only.
C. Flexner et al., *Virology* 166:339–349 (Oct. 1988). Abstract Provided Only.
G. Mazzara et al. in *Modern Approaches to Vaccines*, Cold Spring Harbor Laboratory, New York (1987).
D. Gheysen et al. in *Modern Approaches to New Vaccines*, Cold Spring Harbor Laboratory, New York, Sep. 14–18, 1988, Abstract No. 72.
D. Gheysen et al., *Cell* 59:103 (1989).

*Primary Examiner*—Mindy Fleisher
*Assistant Examiner*—Johnny F. Railey, II
*Attorney, Agent, or Firm*—Sewall P. Bronstein; Ronald I. Eisenstein; David S. Resnick

[57] ABSTRACT

Recombinant viral vectors which coexpress heterologous polypeptides capable of assembling into defective nonself-propagating viral particles are disclosed. The viral vectors as well as the viral particles can be used as immunogens and for targeted delivery of heterologous gene products and drugs.

12 Claims, 3 Drawing Sheets

SELF-ASSEMBLED, DEFECTIVE, NON-SELF-PROPAGATING LENTIVIRUS PARTICLES

GOVERNMENT SUPPORT

Work described herein was funded by Grant No. AI26507-01A1 from the National Institute of Allergy and Infectious Diseases. The government has certain rights in this invention.

This invention was made with Government support under NIH No. A126507. The Government has certain rights in this invention.

RELATED APPLICATION

This is a continuation of application Ser. No. 07/540,109 filed on 6/19/90, now abandoned. Application Ser. No. 07/540,109 is a continuation-in-part of U.S. Ser. No. 07/360,027, filed Jun. 1, 1989, now abandoned, which is a continuation-in-part of U.S. Ser. No. 07/205,454, filed Jun. 10, 1988 now abandoned. The teachings of each application are incorporated herein by reference.

BACKGROUND

Recombinant approaches have been used in attempts to develop vaccines against diseases for which no vaccine currently exists, or for which conventional vaccine approaches are less desirable. For example, since the human immunodeficiency virus (HIV) was first identified as the etiologic agent of Acquired Immuno-deficiency Disease Syndrome (AIDS), (Barre-Sinoussi et al. *Science* 220:868 (1983); Levey et al., *Science* 225:840 (1984); Gallo et al., *Science* 224:500 (1984)), considerable effort has been directed towards the development of a safe and effective vaccine.

The human immunodeficiency viruses, HIV-1 and HIV-2, are members of the lentivirus subclass of retroviruses. Gonda et al., *Science* 227:173 (1985); Sonigo et al., *Cell* 42:369 (1985). The virus particles contain an inner core comprised of capsid proteins (encoded by the viral gag gene) that encase the viral RNA genome. Rabson & Martin, *Cell* 40:477 (1985). The central core is surrounded by a lipid envelope that contains the viral-encoded envelope glycoproteins. Virus-encoded enzymes required for replication, such as the reverse transcriptase and integrase (encoded by the pol gene), are also incorporated into the virus particle.

There are obvious difficulties with the use of whole virus for an HIV vaccine. The fear that an attenuated virus could revert to virulence, and the danger of incomplete inactivation of killed virus preparations, together with the reluctance to introduce the HIV genome into seronegative individuals have argued against the uses of live attenuated or killed HIV vaccines for the prevention of infection.

Advances in recombinant DNA technology may make it possible to use heterologous expression systems for the synthesis not only of individual antigens, but also of defective, nonself-propagating, virus-like particles. It has been demonstrated that capsid proteins of certain viruses can assemble into particles morphologically and immunologically similar to the corresponding virus. For example, the P1 precursor of several picornaviruses synthesized in vitro can be processed into individual capsid proteins which then assemble into immunoreactive virion-like particles. Nicklin al., *Biotechnology* 4:33 (1986); Palmenberg et al., *J. Virol.* 32:770 (1979); Shih et al., *Proc. Natl. Acad. Sci. USA* 75:5807 (1978); Hanecak et al., *Proc. Natl. Acad. Sci. USA* 79:3973 (1982); Grubman et al., *J. Virol.* 56:120 (1985). Self-assembly of capsid proteins expressed in vivo in several recombinant expression systems has also been reported. For example, when human hepatitis B surface antigen is expressed in yeast cells, the polypeptide assembles into particles similar in appearance to those isolated from human plasma (Valenzuela et al., *Nature* 298:347 (1982)); these particles stimulate anti-hepatitis B antibody production in several species and can protect chimpanzees from virus challenge. McAleer et al., *Nature* 307:178 (1984).

In another example, it was shown that coexpression of canine parvovirus (CPV) capsid proteins VP1 and VP2 in murine cells transformed with a bovine papilloma virus/CPV recombinant plasmid resulted in the formation of self-assembling virus-like particles (Mazzara et al., 1986, in *Modern Amproaches to Vaccines,* Cold Spring Harbor Laboratory, N.Y.; R. M. Chanock and R. A. Lerner, eds. pp. 419–424; Mazzara et al., U.S. patent application Ser. No. 905,299, filed Sep. 8, 1986); when used to vaccinate susceptible dogs, these empty capsids elicited immune responses capable of protecting against CPV challenge. It has also been shown that the HIV-1 and SIV p55gag precursor polypeptides expressed in *Spodoptera frugiperda* cells using a baculovirus expression vector assembles into virus-like particles which are secreted into the cell culture medium. Gheysen et al., *Cell* 59:103 (1989); Delchambre et al., *The EMBO J.* 8:2653–2660 (1989).

SUMMARY OF THE INVENTION

This invention pertains to recombinant viral vectors capable of expressing at least two different polypeptides of a heterologous virus capable of self-assembly, in vivo or in vitro, into defective, non-self propagating viral particles, and to methods of producing the recombinant virus. Preferably, the viral particles are produced by vaccinia viral vectors that coexpress the env and gag-pol genes of HIV. This invention also pertains to intermediate DNA vectors which recombine with a parent virus in vivo or in vitro to produce the recombinant viral vector, and to methods of vaccinating a host with the recombinant viral vector to elicit protective immunity against the correlate heterologous pathogenic virus. In addition, this invention pertains to defective, non-self-propagating viral particles, such as lentivirus or picornavirus particles, produced by the recombinant viral vectors. These viral particles may be isolated and used themselves as immunogens or in combination with other immunogens for vaccination against pathogenic viruses, or for therapeutic purposes, such as enhancing immune responses in an infected individual, or for targeted delivery of heterologous nucleic acids and/or therapeutic agents, such as cytotoxic drugs, to specific cell types. The viral particles can have substantially little or no RNA packaged within the particle; or they can contain specific RNA for delivery of heterologous genes to a targeted cell.

DETAILED DESCRIPTION OF THE INVENTION

1. Genes encoding viral antigens

Figure 1A:
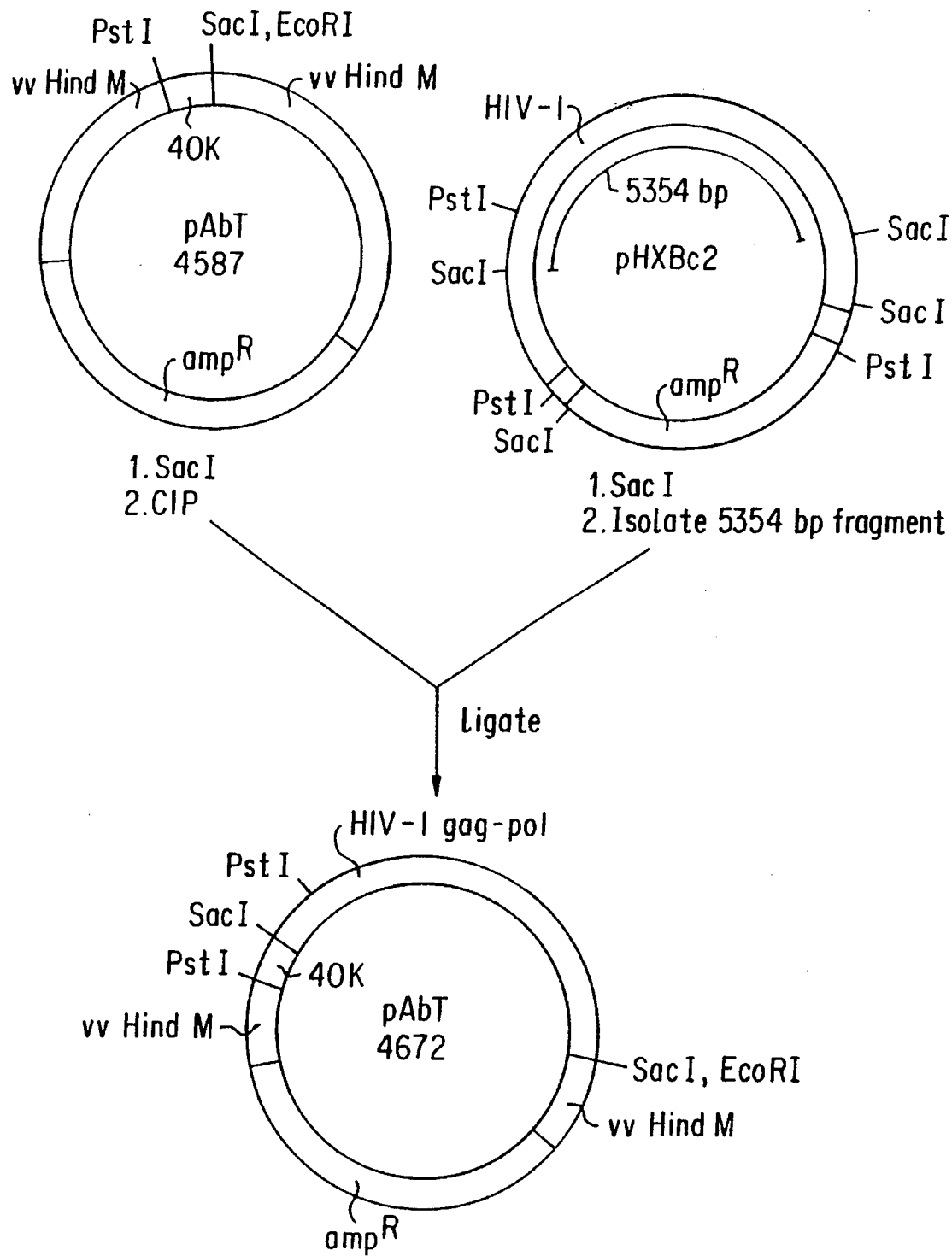
FIG. 1a shows the construction of plasmid pAbT4672 containing the HIV-1 gag-pol gene under the control of the vaccinia 40K promoter.

Genes encoding viral polypeptides capable of self assembly into defective, nonself-propagating viral particles can be obtained from the genomic DNA of a DNA virus or the genomic cDNA of an RNA virus or from available subgenomic clones containing the genes. These genes will include those encoding viral capsid proteins (i.e., proteins that comprise the viral protein shell) and, in the case of enveloped viruses, such as retroviruses, the genes encoding viral envelope glycoproteins. Additional viral genes may also be required for capsid protein maturation and particle self-assembly. These may encode viral proteases responsible for processing of capsid protein or envelope glycoproteins.

As an example, the genomic structure of picornaviruses has been well characterized, and the patterns of protein synthesis leading to virion assembly are clear. Rueckert, R. in *Virology* (1985), B. N. Fields et al. (eds.) Raven Press, New York, pp 705–738. In picornaviruses, the viral capsid proteins are encoded by an RNA genome containing a single long reading frame, and are synthesized as part of a polyprotein which is processed to yield the mature capsid proteins by a combination of cellular and viral proteases. Thus, the picornavirus genes required for capsid self-assembly include both the capsid structural genes and the viral proteases required for their maturation.

Another virus class from which genes encoding self-assembling capsid proteins can be isolated is the lentiviruses, of which HIV is an example. Like the picornaviral capsid proteins, the HIV gag protein is synthesized as a precursor polypeptide that is subsequently processed, by a viral protease, into the mature capsid polypeptides. However, the gag precursor polypeptide can self-assemble into virus-like particles in the absence of protein processing. Gheysen et al., *Cell* 59:103 (1989); Delchambre et al., *The EMBO J.* 8:2653–2660 (1989). Unlike picornavirus capsids, HIV capsids are surrounded by a loose membranous envelope that contains the viral glycoproteins. These are encoded by the viral env gene.

The examples illustrate the use of HIV genes selected for expression in recombinant viruses of this invention. These genes and their protein products are outlined in Table 1. The three major virion components derived from the env, gag, and pol genes are synthesized as precursor polyproteins which are subsequently cleaved to yield mature polypeptides as outlined in Table 1.

TABLE 1

| HIV Genes for Recombination into Pox Virus | | | |
|---|---|---|---|
| Gene | Gene Product | Processed Peptides | |
| env | gp160 | gp120 | extracellular membrane protein |
| | | gp41 | transmembrane protein |
| gag | p55 | p24 | capsid proteins |
| | | p17 | |

TABLE 1-continued

| HIV Genes for Recombination into Pox Virus | | | |
|---|---|---|---|
| Gene | Gene Product | Processed Peptides | |
| pol | p160* | p15 | |
| | | p10 | protease |
| | | p66/p51 | reverse transcriptase |
| | | p31 | endonuclease |

*Part of the gag-pol product.

2. Parent Viruses

A number of viruses, including retroviruses, adenoviruses, herpesviruses, and pox viruses, have been developed as live viral vectors for the expression of heterologous antigens. Cepko et al. *Cell* 37: 1053–1062 (1984); Morin et al., *Proc. Natl. Acad. Sci. USA* 84:4626–4630 (1987); Lowe et al., *Proc. Natl. Acad. Sci. USA* 84:3896–3900 (1987); Panicali & Paoletti, *Proc. Natl. Acad. Sci. USA* 79: 4927–4931 (1982); Mackett et al., *Proc. Natl. Acad. Sci. USA* 79:7415–7419 (1982). The examples given illustrate the use of the pox virus family. The preferred pox virus is vaccinia virus, a relatively benign virus which has been used for years as a vaccine against smallpox. Vaccinia virus has been developed as an infectious eukaryotic cloning vector (Paoletti and Panicali, U.S. Pat. No. 4,603,112) and recombinant vaccinia virus has been used successfully as a vaccine in several experimental systems. The virus is considered non-oncogenic, has a well-characterized genome, and can carry large amounts of foreign DNA without loss of infectivity. Mackett, M. and G. L. Smith, *J. Gen. Virol.* 67:2067 (1986). Another preferred pox virus is fowl pox virus, a pathogen of poultry. This virus has also been developed into a eukaryotic cloning vector. Boyle et al., *Gene* 35:169–177 (1985); U.S. patent application Ser. No. 07/398,762, filed Aug. 25, 1989.

3. DNA vectors for in vivo recombination with a parent virus

According to the method of this invention, viral genes that code for polypeptides capable of assembly into viral particles are inserted into the genome of a parent virus in such as manner as to allow them to be expressed by that virus along with the expression of the normal complement of parent virus proteins. This can be accomplished by first constructing a DNA donor vector for in vivo recombination with a parent virus.

In general, the DNA donor vector contains the following elements:

a) a prokaryotic origin of replication, so that the vector may be amplified in a prokaryotic host;

b) a gene encoding a marker which allows selection of prokaryotic host cells that contain the vector (e.g., a gene encoding antibiotic resistance);

c) at least two heterologous viral genes (e.g., HIV or picornavirus genes), each gene located adjacent to a transcriptional promoter (e.g., the vaccinia 7.5K, 30K, 40K, 11K or BamF promoters or modified versions of these promoters) capable of directing the expression of adjacent genes; and d) DNA sequences homologous to the region of the parent virus genome where the foreign gene(s) will be inserted, flanking the construct of element c (e.g., the vaccinia TK or HindIII M sequences).

Methods for constructing donor plasmids for the introduction of multiple foreign genes into pox virus are described in U.S. patent application Ser. No. 910,501, filed Sep. 23, 1986, which corresponds to EP 026/940 entitled "Pseudorabies Vaccine", the techniques of which are incorporated herein by reference. In general, all viral DNA fragments for construction of the donor vector, including fragments containing transcriptional promoters and fragments containing sequences homologous to the region of the parent virus genome into which foreign genes are to be inserted, can be obtained from genomic DNA or cloned DNA fragments.

The donor vector preferably contains an additional gene which encodes a selectable marker under control of a separate promoter which will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., *J. Virol.* 62:1046 (1988); Falkner and Moss., *J. Virol.* 62:1849 (1988); Franke et al., *Mol. Cell. Biol.* 5:1918 (1985)), as well as genes, such as the *E. coli* lacZ gene, that permit identification of recombinant viral plaques by colorimetric assay. Panicali et al., *Gene* 47:193–199 (1986).

A method for the selection of recombinant vaccinia viruses relies upon a single vaccinia-encoded function, namely the 29K host-range gene product. Gillard et al. *Proc. Natl. Acad. Sci. USA.* 83:5573 (1986). This method was described in U.S. patent application Ser. No. 205,189, filed Jun. 20, 1988, which corresponds to WO 89/1263 entitled "Methods of Selecting for Recombinant Pox Viruses", the teachings of which are incorporated herein by reference.

4. Integration of foreign DNA sequences into the viral genome and isolation of recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603,112).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK⁻ and can be selected on this basis (Mackett et al., 1982, *Proc. Natl. Acad. Sci. USA* 79:7415). Alternatively, co-integration of a gene encoding a marker or indicator gene with the foreign gene(s) of interest, as described above, can be used to identify recombinant progeny. One preferred indicator gene is the *E. coli* lacZ gene: recombinant viruses expressing beta-galactosidase can be selected using a chromogenic substrate for the enzyme (Panicali et al., 1986, *Gene* 47:193). A second preferred indicator gene for use with recombinant vaccinia virus is the vaccinia 29K gene: recombinant viruses that express the wild type 29K gene-encoded function can be selected by growth on RK13 cells. Another method by which recombinant viruses containing genes of interest can be identified is by an in situ enzyme based immunoassay in which protein expressed by vaccinia-infected cells is detected by the formation of live black plaques.

As described more fully in the Examples, donor plasmids containing HIV genes were recombined into vaccinia at the HindIII M region and recombinant viruses were selected as described above.

5. Characterizing the viral antigens expressed by recombinant viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA). Antibodies to antigens expressed by viral pathogens are either readily available, or may be made according to methods known in the art. For example, for human immunodeficiency virus, the antibodies can be either sera from human patients infected with HIV, or commercially available monoclonal antibodies directed against specific HIV polypeptides.

6. Viral Particle formation

Expression analysis described in the preceding section can be used to confirm the synthesis of the polypeptides encoded by inserted heterologous viral genes, but does not address the question of whether these polypeptides self-assemble, in vivo or in vitro, into defective viral particles. Two experimental approaches can be used to examine this issue.

The first approach is to visually examine by electron microscopy lysates of cells infected with recombinant viruses that express one or more viral polypeptides. The presence of retroviral envelope glycoproteins on the surface of the particles can be demonstrated with immunogold electron microscopy, using a monoclonal antibody directed against one of the envelope glycoproteins.

In order to characterize the defective viral particles produced by recombinant viruses expressing viral polypeptides, these particles can be isolated by high speed centrifugation from the culture medium of cells infected with the recombinant viruses in the presence of [$^{35}$S]-methionine. The pellet resulting from centrifugation of the culture medium can be resuspended and both the pellet and the supernatant can be immunoprecipitated with an appropriate antiserum to analyze the viral polypeptides present in each fraction. For example, in the case of recombinants expressing HIV polypeptides, human anti-HIV antisera (for vaccinia/HIV recombinants) can be used for the analysis.

To further characterize the material in the pellet resulting from centrifugation of the culture medium, the pellet can be resuspended and analyzed on a sucrose gradient. The gradient can then be fractionated and the fractions immunoprecipitated with the appropriate antiserum. These experiments show whether the pellet contains material banding at the density expected for defective viral particles.

These methods can also be used to determine whether expression of viral polypeptides directed by two different viruses present in the same infected cell gives rise to the production of defective viral particles. For example, these experiments can be performed using cells coinfected in vitro with one recombinant expressing gag and a second recombinant expressing env. The simultaneous expression in a single cell of both env and gag polypeptides, whether directed by a single divalent recombinant virus or by two different monovalent viruses, would be expected to result in the formation of defective retroviral particles that contain a protein core comprising gag polypeptides surrounded by an envelope containing virally-encoded envelope glycoproteins.

7. Production of virus-like particles which do not contain RNA

Two approaches can be employed to produce "empty" virus-like particles having substantially little or no RNA packaged within the capsid. Such particles may provide greater potential safety for use as a subunit vaccine because the level of viral RNA is reduced, particularly in the case of HIV-like particles.

The first approach involves the removal of gag-specific sequences responsible for recognition of RNA. Using standard molecular biology techniques, it is possible to generate DNA virus recombinants, such as pox virus, that contain and express HIV-1 gag genes having point or deletion mutations in the nucleocapsid domain of the gag protein. For example, pox virus-expressed mutant gag gene products produced by this method will retain the ability to assemble into virus-like particles, but will substantially lack the ability to package mRNA containing the packaging sequence. This approach is based upon previous findings that all retroviruses contain, in the nucleocapsid domain of the gag protein, at least one copy of the sequence Cys-$X_2$-Cys-$X_4$-His-$X_4$-Cys which is involved in the recognition of genomic RNA. Point and deletion mutations generated in this motif in HIV-1 (Gorelick et al., *J. Cell Biochem., Suppl.* 14D:150 (1990)) and Moloney MuLV (Gorelick et al., *Proc. Natl. Acad. Sci. USA* 85:8420 (1988)) demonstrate that the mutant viruses produce viral particles deficient in genomic RNA. Thus, similar point or deletion mutations can be used to generate pox virus recombinants capable of producing empty viral-like particles of this invention.

The second approach is to remove the cis-acting packaging sequences from the gag-pol mRNA. These cis-acting sequences which are located between the 5'LTR and the gag gene initiation codon in avian and murine retroviruses are essential for efficient packaging of viral RNA into virions. A sequence required for effective packaging of the HIV-1 genome RNA in viral particles was recently identified. Lever et al., *J. Virol.* 63:4085 (1989). Lever et al. demonstrated that deletion of 19 base pairs between the 5' LTR and the gag gene initiation codon of HIV-1 resulted in the generation of a mutant virus markedly attenuated for replication in human T lymphocytes. The mutant virus was characterized by nearly wild-type ability to encode viral proteins and to produce virion particles. These virion particles exhibited a significant reduction in the content of HIV-1 specific RNA.

The vaccinia recombinants shown in the Examples (vAbT408) encode a gag-pol mRNA that contains the putative packaging sequence identified by Lever et al. However, it is possible to generate pox virus recombinants that contain and express the gag-pol coding sequence but which do not contain, as part of the inserted gene, the cis-acting packaging sequences 5' to the start of the gag initiation codon. Such a recombinant pox virus should retain the ability to produce HIV-1 virus-like particles, since it will express the entire gag structural gene sequence. These particles, however, should contain significantly lower levels of HIV-1 specific RNA as compared to particles produced by recombinants which expresses an mRNA that contains this cis-acting packaging sequence, such as recombinant vAbT408 shown in the Examples.

8. Production of virus-like particles that contain a specific expressible RNA that can be reverse transcribed.

Alternatively, it may be preferable to produce a capsid that contains a specific RNA packaged therein. Such capsids can be used to deliver specific RNA to cells targeted by the particles (i.e., HIV-infectible cells). Preferably, this can be done by minimizing the level of gag-pol messenger RNA packaged in the capsids and at the same time encoding the desired RNA species, in a recombinant DNA virus (the same one in a multivalent formulation, or a different one for use in coinfection), such as pox virus.

Using standard techniques, it is possible to design a recombinant that produces particles 1) containing an RNA of choice; 2) capable of targeting HIV-1 infectible cells; 3) capable of delivering the RNA to those cells; 4) capable of reverse transcribing that RNA into DNA which can integrate into the genome of the targeted cell. The packaged RNA species should contain the HIV LTRs, so that it can be reverse-transcribed by the reverse transcriptase contained in the particle into DNA, and that DNA should be capable of integrating into the host genome. The RNA of choice should also contain the cis-acting packaging sequence and a gene of interest under the transcriptional control of either the HIV-1 LTRs or of a heterologous eukaryotic promoter (e.g., the CMV IE or the SV40 promoter).

One way to produce such an RNA in pox virus-infected cells is to insert the appropriate sequences into pox virus under the transcriptional control of a pox virus promoter (alternatively, the sequences, under the transcriptional control of a pox promoter, can be carried on a plasmid that is transfected into pox virus-infected cells). The construct to be expressed in pox virus-infected cells should have the following elements: 1) sequences capable of encoding an RNA containing (in the 5' to 3' orientation) the leftward HIV-1 LTR, the cis-acting packaging sequences, the gene of interest (or, a eukaryotic promoter linked to the gene of interest) and the rightward HIV-1 LTR; 2) these sequences should be under the transcriptional control of a pox virus early promoter and linked to this promoter in such a way that the RNA cap site specified by the pox virus promoter coincides with the authentic RNA cap site of HIV-1; 3) these sequences should be flanked at the 3' terminus by a pox virus RNA termination sequence (TTTTTNT), if it is desirable, so that an RNA of a discrete length is encoded. For insertion into recombinant pox virus, elements 1–3 should be flanked by sequences homologous to a non-essential region of the pox virus genome, to permit insertion of these sequences into the genome by homologous recombination in vivo. Production of this RNA in cells infected by a recombinant pox virus capable of directing the formation of HIV-1 virus-like particles which contain env, gag and pol gene products will result in the production of particles that contain the inserted RNA of interest. It may be possible to maximize the proportion of particles containing the desired RNA by using a pox virus recombinant which does not package substantial amounts of the mRNA encoding the gag-pol genes by using certain drugs, such as araC, which permit RNA synthesis only from early vaccinia promoters; and/or by using recombinant vaccinia viruses which contain conditionally lethal mutations that prevent the synthesis of late RNA.

9. Production of virus-like particles that contain a specific expressible RNA that cannot be reverse transcribed.

It may be desirable to package RNA that can, when delivered to the target cell, be translated directly by the cell rather than integrated into the cellular DNA. For example, RNA encoding a highly active toxin might be delivered in a virus-like particle as translatable mRNA. To produce particles containing non-integrating mRNA, the recombinant can be designed essentially as described in 8, above, except that neither the HIV-1 LTRs nor the heterologous eukaryotic promoter are included in the construction. All other elements of the construction are identical. Without the LTRs, the RNA cannot be reverse transcribed and will be available to the cell for translation into protein.

10. Vaccines

Live recombinant viral vectors that express heterologous viral antigens capable of self-assembly into defective non-self-propagating virus particles can be used to vaccinate humans or animals susceptible to infection if the viral vector used to express the heterologous defective virus particles infects but does not cause significant disease in the vaccinated host. Examples of such benign viral vectors include certain pox viruses, adenoviruses, and herpes viruses. For example, vaccination with live recombinant vaccinia virus is followed by replication of the virus within the host. During replication, the viral genes are expressed along with the normal complement of recombinant virus genes. Thus, during the two-week postimmunization period when the live recombinant virus is replicating (Fenner, F., in *Virology*, Fields et al., eds. Raven Press, New York, 1985, pp 661–684), viral antigens may be presented to the host immune system in a manner that closely mimics the presentation of antigens in an authentic viral infection, that is, as defective, non-self-propagating viral particles extremely similar to the native virus. Viral antigens repeatedly presented both as free particles and in association with recombinant virus-infected cells may have the potential to prime the immune system to recognize and eliminate the virus during the early events of viral infection.

Alternatively, the defective virus particles produced by these recombinant vector viruses can be isolated from cells infected in vitro with the recombinant vector viruses and from the culture medium of these infected cells, and themselves used for vaccination of individuals susceptible to viral infection. These particles resemble the native virus, but will not contain infectious viral genetic material, such as HIV mRNA. Consequently, they offer the advantage of conventional killed virus vaccine preparations: the ability authentically to present immunogenic antigens to the immune system of the vaccinated host. At the same time such particles circumvent the major drawbacks to the use of killed virus as a vaccine for the prevention of infection, including the danger of incomplete inactivation of killed virus preparations and, as for the case of certain viruses, such as retroviruses, the reluctance to introduce a complete viral genome (the HIV genome, for example) into seronegative individuals.

Vaccine compositions utilizing these defective virus particles would generally comprise an immunizing amount of the viral particles in a pharmaceutically acceptable vehicle. The vaccines would be administered in a manner compatible with the dosage formulation, and in such amount as would be therapeutically effective and immunogenic.

Finally, the purified particles may be used in combination with live recombinant viruses as part of a total vaccination protocol, either as the primary immunizing agent, to be followed by vaccination with live recombinant virus, or to boost the total immune response after primary vaccination with live recombinant virus.

11. Therapeutic use of recombinant viruses expressing viral antigens capable of assembling into defective viral particles; therapeutic use of defective viral particles produced by these recombinant viruses Even if immunization can not protect against infection, immunization of a previously infected individual might prolong the latency period of that virus within the individual. This may be particularly important in the case of viral infections characterized by long latency periods, such as HIV infection. The long incubation time between HIV infection and the development of clinical AIDS may be due to an immune response to the initial infection which persists with health and wanes with disease. If this is the case, boosting the immune response by immunization with HIV antigen/parent virus recombinants that produce retro-viral-like particles, or alternatively, with the purified particles themselves, may prevent the development of disease and reduce contagiousness. Salk, *Nature* 327:473 (1987).

The defective viral particles of this invention can also be used to deliver heterologous genes (e.g., antisense genes, mutant HIV genes) to a targeted cell. Specific RNA packaged within the defective viral particle can then be transcribed by the targeted cells. For example, the viral particle can contain a specific RNA that when transcribed is toxic to the targeted cell, which might be for example HIV-infected cells.

Viral particles containing RNA encoding heterologous genes can be administered to an individual to produce an immune response to the viral particles, as well as to deliver the heterologous gene products.

12. Therapeutic use of defective virus particles as agents for targeted drug delivery Defective, nonself-propagating virus particles can also be used to deliver certain drugs (e.g. cytotoxic drugs, antiviral agents, nucleic acids) to virus receptor-bearing cells. Such drugs may be coupled, by techniques known in the art, to the outer surface of the virus particle, or incorporated within, and delivered with high specificity to target cells. For example, cytotoxic drugs may be coupled to defective HIV particles and delivered with a high degree of specificity to $CD4^+$ T cells, since the HIV envelope glycoprotein present on these particles binds specifically and with high affinity to the CD4 molecule. Similarly, poliovirus particles, for example, preferentially bind cells of the nasopharynx and gut, and thus can be used to direct delivery of specific agents to these or other cells that have poliovirus receptors.

13. Diagnostic uses of virus-like particles

Immunogenic virus-like particles can be used to diagnose viral infection. The particles can be used to raise a panel of monoclonal antibodies and polyclonal antisera which recognize various epitopes on the virion. These monoclonal and/or polyclonal antibodies can be used individually or together as capture antibodies for an immunoassay to detect the presence of virus in urine, blood, or other physiological samples.

Alternately, the particles themselves can be used as antigens for an immunoassay to detect the presence of antibody in urine, blood, or other physiological samples. Particularly preferred immunoassays are solid phase immunometric assays (enzymetric, radiometric). In such assays, the virus-like particle is immobilized on a solid phase to provide an immunoadsorbent. The techniques for use of solid phase immunoadsorbents are known in the art.

This invention is illustrated further by the following examples:

EXAMPLES

GENERAL PROCEDURES

Cells and Virus

*E. coli* strain MC1061 (Casadaban and Cohen, *J. Mol. Biol.* 138:179 (1980)) was used as the host for the growth of all plasmids. The monkey kidney cell line BSC-40 (Brockman & Nathans, *Proc. Natl. Acad. Sci. USA* 71:942 (1974)) and the rabbit kidney cell line RK13 (ATCC #CCL37; Beale et al., *Lancet* 2:640 (1963)) were used for vaccinia infections and transfections. Cells were propagated in Dulbecco modified Eagles Medium (DME, Hazelton, Lexena, Kans.) supplemented with 5% fetal calf serum (FCS. Hyclone Laboratories, Inc., Logan, Vt.).

A plaque purified isolate of the Wyeth strain of vaccinia virus was obtained from Flow Laboratories (McLean, Va.). This virus and 29K– lacZ+ strain vAbT33 (see U.S. patent application Ser. No. 205,189, filed Jun. 10, 1988, which corresponds to WO89/12/03 incorporated herein by reference) were used as the parental virus for in vivo recombination. Viral infection, transfections, plaque purification and virus amplification were performed essentially as described. Spyropoulos et al., *J. Virol.* 62:1046 (1988).

Molecular Cloning Procedures

Restriction enzyme digestions, purification of DNA fragments and plasmids, treatment of DNA with Klenow, T4 DNA polymerase, calf intestinal alkaline phosphatase, T4 DNA ligase, or linkers and transformation of *E. coli* were performed essentially as described (Maniatis et al., Molecular Cloning: A Laboratory Manual, Cold Spring Harbor Laboratory, Cold Spring Harbor, N.Y., 1982, the teachings of which are incorporated herein by reference). Restriction enzymes were obtained from New England BioLabs or Boehringer-Mannheim. The large fragment of DNA polymerase (Klenow) was obtained from United States Biochemical Corporation, T4 DNA polymerase was obtained from New England BioLabs, and T4 DNA ligase and calf intestinal alkaline phosphatase were obtained from Boehringer-Mannheim.

EXAMPLE 1

Construction of recombinant plasmid for in vivo recombination with vaccinia virus containing the HIV env gene under the control of the vaccinia D1 promoter and the HIV gag-pol genes under the control of the vaccinia 40K promoter.

pHXBc2 is a plasmid that contains portions of the HIV-1 strain HXB2 genome; it was obtained from Dr. Joseph Sodroski of the Harvard Medical School. The construction and structure of plasmid pAbT4587 is described in U.S. patent application Ser. No. 229,343, filed Aug. 5, 1988 which correponds to WO90/0/546. The construction and structure of plasmid pAbT4603 was described in U.S. patent application Ser. No. 360,027, filed Jun. 1, 1989 which corresponds to WO90/15141. The teachings of these applications are incorporated herein by reference.

pAbT4674 (FIG. 1).

a. Construction of pAbT4672 (FIG. 1a).

Figure 1B:
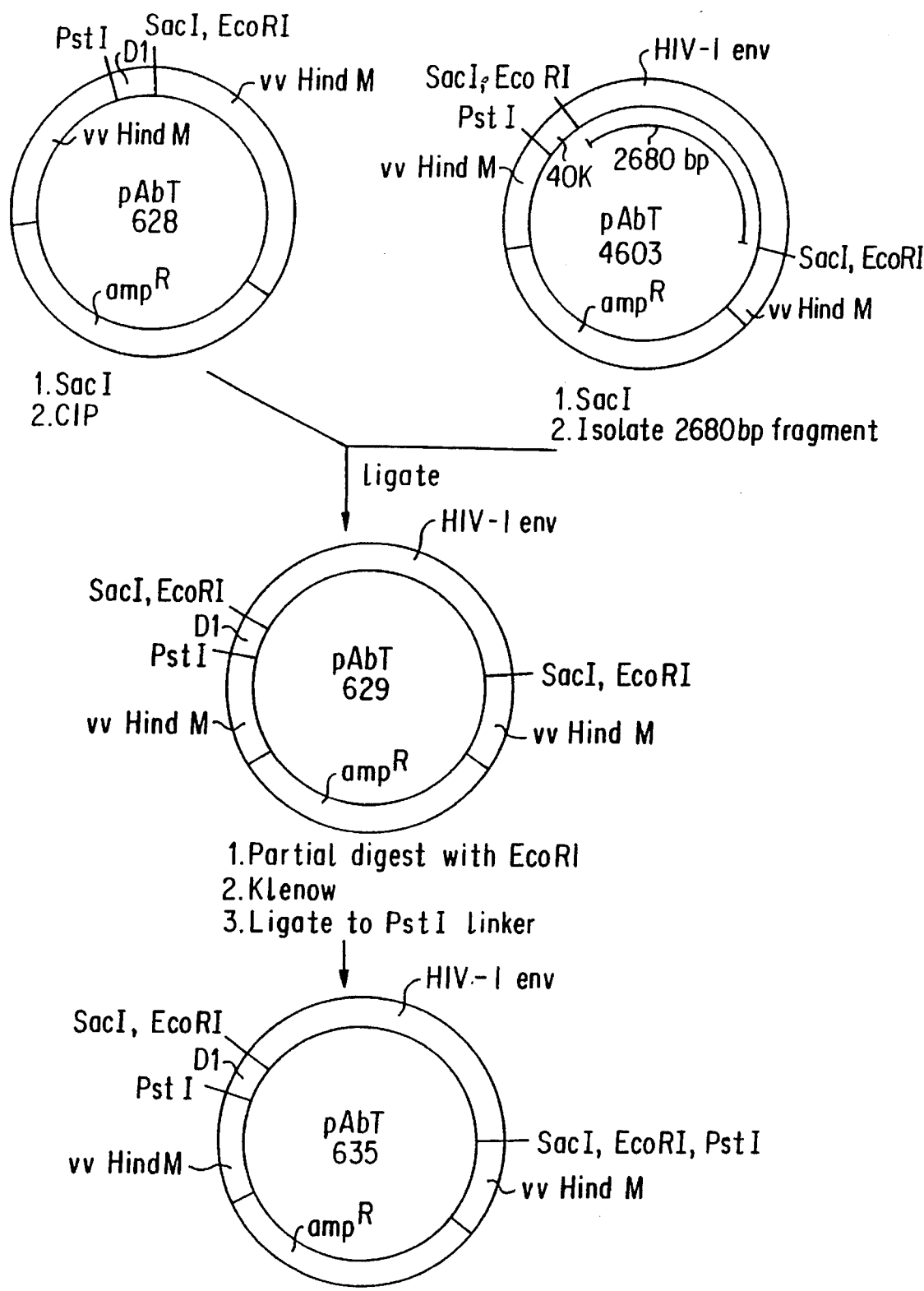
FIG. 1b shows the construction of plasmid pAbT635 containing the HIV-1 env gene under the control of the vaccinia D1 promoter.

Plasmid pAbT4587 was digested with Sac I and treated with calf intestinal alkaline phosphatase (CIP). This vector was ligated to a 5354 bp fragment produced by digesting pHXBc2 with Sac I, to yield plasmid pAbT4672.

b. Construction of pAbT635 (FIG. 1b).

Plasmid vector pAbT4587 contains the vaccinia 40K promoter. Rosel, *J. Virol.* 60:436 (1986). Plasmid pAbT628 is identical to plasmid pAbT4587, except that it contains, in place of the 40K promoter, a DNA fragment with the following nucleotide sequence between the unique PstI and Bam HI sites in the vector:

PstI CTGCAGCAGC TTAAAATAGC TCTAGCTAAA GGCATAGATT ACGAATATAT AAAAGACGCT TGTTAATAAG TAAATGAAAA AAAACTAGTC GTTTATAATA BamHI AAACACGATA TCTAGAGGAT CC

Figure 1C:
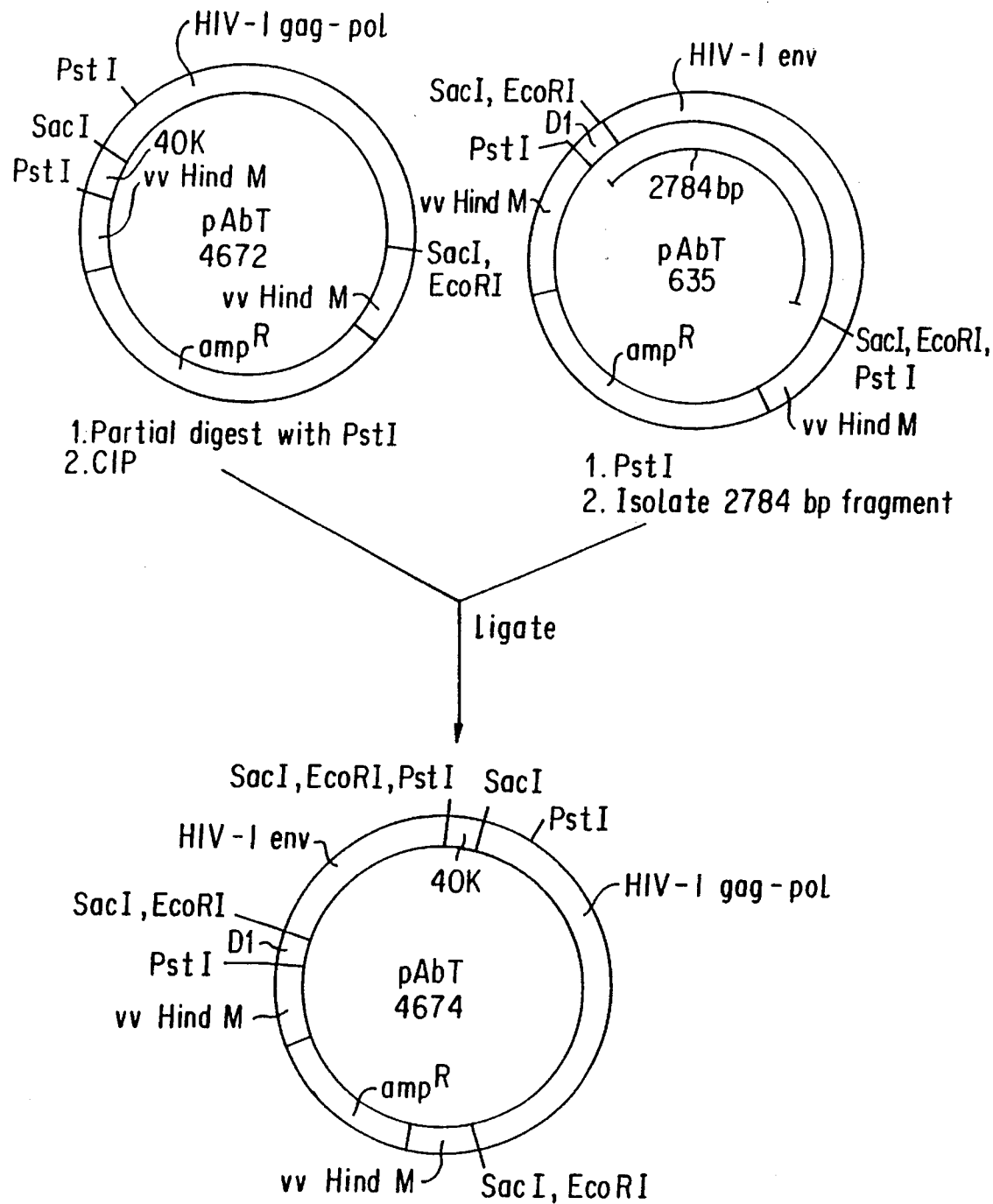
FIG. 1c shows the construction of pAbT4674, a plasmid vector for the insertion and expression of HIV gag-pol (strain HXB2) and env (strain BH10) in vaccinia virus. pAbT4674 contains the gag-pol gene under the control of the vaccinia 40K promoter and the env gene under the control of the vaccinia D1 promoter.

This DNA fragment contains vaccinia DNA sequences corresponding to the D1 promoter (Niels et al., *Virology* 153:96 (1986)), indicated by the underline, modified by the addition of linkers at each end to facilitate cloning into the plasmid vector. pAbT628 was digested with SacI, then treated with CIP. This vector was ligated to an approximately 2680 bp fragment containing the HIV env gene from HIV-1 strain BH10, which was produced by digestion of pAbT4603 with SacI, to yield plasmid pAbT629. Plasmid pAbT629 was partially digested with EcoRI, then ligated to an oligonucleotide linker containing a PstI site (New England BioLabs, Beverly, Ma., cat. #1013). The resulting plasmid was designated pAbT635.

c. Construction of pAbT4674 (FIG. 1c).

Plasmid pAbT635 was digested with PstI, and a 2784 bp fragment resulting from this digestion was purified. This fragment was ligated to the products of limited digestion of pAbT4672 with PstI, to produce the plasmid pAbT4674, which is a vector for the insertion and expression of HIV gag-pol (strain HXB2) and env (strain BH10) in vaccinia virus. pAbT4674 contains the gag-pol gene under the control of the vaccinia 40K promoter (Rosel, *J. Virol.* 60:436 (1986)), and the env gene under the control of the vaccinia D1 promoter. Niels et al. *Virology* 153:96 (1986). The HIV genes and their adjacent vaccinia promoters are flanked by vaccinia DNA for directing recombination into the vaccinia HindIII M region. The vector DNA includes the 29K host-range gene for selection of vaccinia recombinants and a bacterial replicon and ampicillin-resistance gene for growth and selection in *E. coli*.

EXAMPLE 2

Construction of recombinant vaccinia viruses containing the HIV-1 (strain BH10) env gene under the control of the vaccinia D1 promoter and the HIV-1 (strain HXB2) gag-pol genes under the control of the vaccinia 40K promoter.

In vivo recombination (IVR) is a method whereby recombinant vaccinia viruses are created. Nankano et al., *Proc. Natl. Acad. Sci. USA* 79:1593 (1982); Paoletti and Panicali, U.S. Pat. No. 4,603,112. These recombinant viruses are formed by transfecting DNA containing a gene of interest into cells which have been infected by vaccinia virus. A small percent of the progeny virus will contain the gene of interest integrated into a specific site on the vaccinia genome. These recombinant viruses can express genes of foreign origin. Panicali and Paoletti, *Proc. Natl. Acad. Sci. USA* 79:4927 (1982); Panicali et al., *Proc. Natl. Acad. Sci. USA* 80:5364 (1983).

a. Insertion of HIV-1 genes into vaccinia strain vAbT33.

To insert HIV-1 genes into the vaccinia virus genome at the HindIII M region of vaccinia virus strain vAbT33, a selection scheme based upon the 29K host-range gene, which is located in this region, was used. Gillard et al., *Proc. Natl. Acad. Sci. USA* 83:5573 (1986). Recombinant vaccinia virus vAbT33 contains the lacZ gene in place of a portion of the 29K gene. This lacZ insertion destroys the function of the 29K gene; therefore, vAbT33 grows poorly on RK-13 cells, which require the 29K gene product. Furthermore, vAbT33 forms blue plaques on permissive cells in the presence of the chromogenic substrate for β-galactosidase, Bluogal, due to the presence of the lacZ gene. See U.S. patent application Ser. No. 205,189, filed Jun. 10, 1988 which corresponds to WSO89/12103.

IVR vector pAbT4674 was transfected into BSC-40 cells which had been infected with vaccinia virus vAbT33. Viral infection and plasmid transfection were performed essentially as described. Spyropoulos et al., *J. Virol.* 62:1046 (1988). Recombinant viruses were selected as white plaques in the presence of Bluogal on RK-13 cells. Plaques were picked and purified, and the final recombinant, designated vAbT408, was amplified on RK-13 cells and purified over a 36% sucrose cushion.

b. Insertion of HIV-1 genes into the Wyeth strain of vaccinia virus.

In order to insert HIV-1 genes in the vaccinia virus genome at the HindIII M region of the Wyeth vaccinia virus strain, a procedure based on an in situ enzyme-based immunoassay (live black plaque selection) which can detect protein expressed by vaccinia-infected cells was used. Following in vivo recombination on RK-13 cells for 48 hours, RK-13 cells were infected with the viral progeny, and plaques were allowed to form. The cell monolayer was then fixed with 3.7% formaldehyde for 5 minutes, washed once with PBS, and then incubated for 60 minutes with a monoclonal antibody specific for the p17 gag protein (Cellular Products, Inc., Buffalo, N.Y., cat. #0801005) diluted in 3% BSA/PBS. After washing three times in PBS, the sample was incubated for 60 minutes with alkaline phosphate labeled goat anti-mouse IgG (Kirkegard & Perry Laboratories, Gaithesberg, Md.) diluted in 3% BSA/PBS, then washed twice with PBS and once with TBS. Color was developed using 5-bromo-4-chloro-3-indolyl phosphate/nitro blue tetrazolium. Positive plaques stain a distinct dark purple color; one plaque was picked and its progeny further propagated. Additional rounds of live black plaque selection were performed on unfixed plaques using IgG purified from serum obtained from HIV-1-infected, human vaccinia naive patients, provided by John Sullivan (University of Massachusetts Medical School, Worcester, Mass.) as a primary antibody and alkaline phosphatase-labeled, affinity purified goat anti-human IgG as the secondary antibody. The isolated recombinant, designated vAbT4674, was amplified on RK-13 cells and purified over a 36% sucrose cushion.

c. Southern blot analysis of vAbT408 and vAbT4674.

DNA was extracted from vaccinia virus-infected cells as described (Esposito et al., 1981, *J. Virol. methods* 2:175) and analyzed by digestion with Hind III and Southern hybridization with radiolabeled probes corresponding to the HIV-1 env or HIV-1 gag-pol genes as described. Maniatis et al., Molecular Cloning: A Laboratory Manual, Cold Spring Harbor Laboratory, Cold Spring Harbor, N.Y. (1982). As expected from the predicted genomic structure of these recombinants, hybridization of the digested DNA with radiolabeled gag-pol genes detected fragments of approximately 4992, 1318 and 617 base pairs (bp), while hybridization with radiolabeled env gene detected fragments of approximately 2877 and 1318 bp. This analysis confirmed the presence of these HIV-1 sequences in the recombinant viruses.

EXAMPLE 3

Immunoprecipitation of HIV-1 antigens from cells infected with recombinant vaccinia viruses.

Metabolic labeling with [$^{35}$S]-methionine of BSC-40 cells infected with recombinant vaccinia viruses vAbT408 and vAbT4674 and subsequent immunoprecipitation analysis was performed essentially as described in U.S. patent application Ser. No. 910,501 filed Sep. 23, 1986 which corresponds to EP 026/940, the teachings of which are incorporated herein by reference. The results, which are summarized in Table 2, show that each of these vaccinia recombinants expresses the encoded polypeptide(s).

TABLE 2

Immunoprecipitation of HIV-1 polypeptides from recombinant vaccinia viruses

| Vaccinia recombinants | Inserted genes | Proteins observed |
| --- | --- | --- |
| vAbT408, vAbT4674 | env, gag-pol | gp160, gp120, gp41 p55, p40, p24, p17 p66, p51, p34 |

EXAMPLE 4

Detection, using radioimmunoprecipitation, of Retro-viral Particles Produced By Vaccinia Recombinants that express HIV antigens.

Expression analysis described in Example 3 can be used to confirm the synthesis of the polypeptides encoded by inserted HIV genes, but does not address the question of whether these polypeptides self-assemble into retroviral-like particles. As one means of determining whether vaccinia recombinants that express both env and gag-pol produce retroviral-like particles released into the medium of infected cells, the medium was examined for the presence of structures containing env, gag and pol polypeptides which could be pelleted by centrifugation. BSC-40 cells were infected with the recombinant viruses and labeled with [$^{35}$S]-methionine as described in Example 3. After 16–18 hours of infection, the medium was collected and clarified by centrifugation twice at 3000 rpm for 5 minutes. The resulting supernatant was then centrifuged at 25,000 rpm for 90 minutes. The supernatant was removed, and the resulting pellet was resuspended in 3 ml PBS buffer (136 mM NACl, 2.7 mM KCl, 8.1 mM Na$_2$HPO$_4$, 1.5 mM KH$_2$PO$_4$). Samples from the supernatant and pellet were subjected to immunoprecipitation analysis using human anti-HIV antiserum, as described in Example 3. The results showed that while the supernatant contained only gp120, which had been presumably shed into the culture medium during growth of the recombinants (Kieny et al., i Bio/Technology 4:790 (1986)), and the encoded p24 polypeptide, the pellet contained not only gp120, but also the env gene-encoded gp41 as well as the gag gene-encoded p55, p40, p24 and p15, and the pol encoded reverse transcriptase and endonuclease. These results strongly suggested that the recombinant vaccinia-produced env, gag and pol proteins self-assemble into particles or complexes.

EXAMPLE 5

Analysis of retroviral particles produced by recombinant vaccinia viruses that express HIV antigens using sucrose density gradient sedimentation.

In order to confirm that vaccinia recombinant vAbT408 directs the expression of retroviral-like particles, particles were harvested from the culture medium of 10 roller bottles of BSC-40 cells infected with these recombinants and subjected to sucrose density gradient sedimentation. Cells were infected with the recombinant vaccinia virus at an moi of 10 pfu per cell for 24 hours in serum-free DME. Culture medium was then collected and clarified to remove cell debris by two centrifugations at 3000 rpm for 10 minutes. The cultured medium was filtered through a 0.2 μm cellulose acetate filter (Nalgene, cat #156-4020), and particles were then pelleted by centrifugation at 25,000 rpm for 90 minutes in a Beckman SW28 rotor and resuspended in 1 ml STE (10 mM Tris, pH 8, 100 mM NaCl, 1 mM EDTA). 400 μl of the particle preparation was reserved for analysis by SDS-polyacrylamide gel electrophoresis, for measurement of reverse transcriptase activity, and for analysis of RNA content; the remaining 600 μl was applied to a 15 ml 15–45% sucrose density gradient and sedimented for 20 hours at 25,000 rmp in a Beckman SW28 roter. Fractions (1 ml) were collected and analyzed by SDS-PAGE followed by protein stain or immunoblot using human anti-HIV antiserum. HIV-specific protein bands, including processed gag polypeptides, reverse transcriptase and endonuclease, and envelope glycoproteins, co-sedimented in the gradient; these results demonstrated that the pelleted material contains retroviral-like particles, rather than simply aggregates of retroviral polypeptides. Fractions were also analyzed for reverse transcriptase activity and for the presence of HIV-specific RNA, as described in the following examples.

EXAMPLE 6

Retroviral-like particles produced by HIV/vaccinia recombinants contain HIV-specific RNAs.

The retroviral-like particles described in Example 5, including both the pellet fraction (starting material) as well as the fractions collected from the sucrose density gradient were analyzed for the presence of HIV-specific RNA and for vaccinia-specific RNA. Particle preparations were treated with SDS and proteinase K, then deproteinized by phenol/chloroform extraction. Nucleic acid released by this procedure was concentrated by ethanol precipitation, resuspended in TE buffer, and applied to nitrocellulose filters for hybridization to radiolabeled DNA probes respresenting the HIV env gene, the HIV gag-pol regions, and the vaccinia TK gene. The results showed that the particles contained nucleic acid which hybridized to both HIV probes used, but not to the vaccinia TK probe.

EXAMPLE 7

Retroviral-like particles produced by recombinant vaccinia viruses contain reverse transcriptase activity.

The retroviral-like particles described in Example 5, including both the pellet fraction (starting material) as well as the fractions collected from the sucrose density gradient were analyzed for the presence of reverse transcriptase (RT) activity. The reaction buffer consisted of 40 mM Tris (pH 7.8), 45 mM KCl, 5 mM $MgCl_2$, 4 m DTT, 0.03% Triton X-100, 25 μg/ml poly rA-oligo dT (Pharmacia cat. #27-7878-02), and 1 uCi $^3$H-TTP (New England Nuclear, cat. #221H, 1.92×10 uCi/mMol). Following incubation at 37° C. for 60 minutes, the reaction was placed on ice, brought to 25 mM EDTA, precipitated with 6% TCA, and filtered through GFC filters (Whatman). The filters were washed 2 times with 2% TCA, once with 100% ethanol, dried, and counted in a Beckman LS 1801 scintillation counter. This assay showed that specific RT activity was present in material pelleted from the culture medium of infected cells. Furthermore, this activity co-sedimented with gag and env polypeptides in the sucrose gradient, as expected for HIV-like particles.

EXAMPLE 8

Production of HIV-retroviral-like particles for use as immunogen.

In order to investigate the utility of HIV-like particles produced by recombinant vaccinia virus as an immunogen, particles were prepared from the culture medium of RK-13 cells infected with vAbT408. Twenty four 15 cm culture dishes of RK-13 cells were infected with vAbT408 at a multiplicity of 10 for 24 hours in serum-free DME. The culture medium was harvested and clarified by two centrifugations at 3000 rpm for 10 minutes, filtered through a 0.45 μm filter (Minitan, cat. #HVLPOMPO4, Millipore Corp., Bedford, Mass.) and applied to a discontinuous (20–36–60%) sucrose gradient. The gradient was centrifuged at 25,000 rpm for 5 hours in a Beckman SW28 rotor, and the region containing HIV-like particles was harvested. Particles were concentrated by centrifugation at 25,000 rpm for 2 hours and resuspended in 1.0 ml of PBS. Total protein in the sample was measured using the BioRad Protein Microassay (BioRad cat. #500-0001) according to the manufacturer's instructions. The presence of retro-viral-like particles in the preparation was determined by SDS-PAGE analysis followed by staining with Coomassie brilliant blue, which showed the presence of the processed gag polypeptides p24 and p17. The sample was treated with 0.8% formalin overnight to inactivate any residual live vaccinia virus present in the particle preparation.

EXAMPLE 9

Immunopotency of recombinant vaccinia virus vAbT408 and of HIV-like particles derived therefrom.

Recombinant virus vAbT408 was shown to be capable of eliciting HIV-specific humoral immune responses in rabbits. In addition, the HIV-like particle preparation described in Example 8 was shown to be capable of boosting the humoral immune response to HIV in rabbits previously immunized with vaccinia recombinant vAbT408.

Each of two New Zealand White Rabbits were immunized intraveneously with 5×10$^7$ pfu of vaccinia recombinant vAbT408. Seventeen weeks after primary immunization with vAbT408, rabbits were boosted with the partially purified particle preparation described in Example 8. Two different adjuvants were used for formulation of the immunogen: complete Freunds adjuvant and alum. Each animal received a total of 5 μg of total particle preparation, administered subcutaneously at five sites on the back. Serum samples were collected at two week intervals after primary inoculation.

To demonstrate that rabbits inoculated with the recombinant vaccinia virus vAbT408 produced antibodies against authentic HIV-1 proteins, serum samples were analyzed by Western immunoblot. Serum samples diluted 500-fold in Blotto (3% milk, 2% normal goat serum, 0.1% Tween™ 20 in PBS) were reacted with HIV-1 virion proteins which had been resolved by SDS-PAGE and immobilized on nitrocellulose filters by electrotransfer (Epiblot™ HIV strips, Organon Teknika Corp., Durham, N.C.). HIV-1 proteins recognized by these sera were detected by goat anti-rabbit immunoglobulin conjugated with alkaline phosphatase (Jackson ImmunoResearch). Both animals immunized with the recombinant virus produced antibodies that reacted with HIV-1 p24 gag protein as early as two weeks post-immunization. Weak reactivity to other HIV-1 proteins, including gp160, p66 (reverse transcriptase), and p32 (endonuclease) was also observed. Three weeks following the boost with the particle preparation, both animals developed readily detectible antibody responses to gag (p55, p24 and p17) and pol (p66/51, p32) polypeptides, with the strongest response observed in the animal immunized with particles formulated in complete Freund's adjuvant.

Plasmid Demosits

The plasmid pAbT4674 was placed on deposit, under provisions of the Budapest Treaty, at the American Type Culture Collection in Rockville, Md. on Jun. 15, 1990. The plasmid has been assigned accession number 70829.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A plasmid vector for insertion of Human Immunodeficiency Virus (HIV) DNA sequences into a pox virus by in vivo recombination, the plasmid vector comprising:

(a) a prokaryotic origin of replication, so that the plasmid vector may be amplified in a prokaryotic host cell;

(b) a gene encoding a marker which allows selection of prokaryotic host cells that contain the plasmid vector;

(c) two DNA sequences from single species HIV, wherein one of the HIV DNA sequences is the env gene and the other of the HIV DNA sequences is the gag-pol gene, such that each gene is operably-linked to a separate eukaryotic transcriptional promoter capable of directing the co-expression of env, gag and pol proteins that self-assemble into a defective, non-self-propagating HIV particle; and (d) pox virus DNA sequences flanking (c), wherein the pox virus DNA sequences are homologous to a region of the genome of a pox virus vector to allow in vivo recombination between the plasmid vector and the pox virus vector, thereby inserting (c) into the pox virus vector.

2. The plasmid vector of claim 1, wherein the gag-pol DNA sequence codes gag proteins deficient in the attachment site for HIV genomic RNA.

3. The plasmid vector of claim 1, wherein the gag-pol DNA sequence has the cis-acting package sequence deleted therefrom.

4. The plasmid vector pAbT4674 having the ATCC designation number 40829, wherein the vector is for insertion of Human Immunodeficiency Virus (HIV) DNA sequences into a pox virus vector by in vivo recombination and the HIV DNA sequences are capable of directing the co-expression of env, gag and pol proteins that self-assemble into a defective, non-self-propagating HIV particle.

5. A pox virus vector having inserted therein, at least two DNA sequences from a single species of lentivirus DNA sequences wherein one of the lentivirus DNA sequences is the env gene, or a portion thereof, and the other of the lentivirus DNA sequences is selected from the group consisting of the gag gene and gag-pol gene or portions thereof, such that the lentivirus DNA sequences express either env, gag, gag-pol proteins, or portions thereof, in a eukaryotic host cell infected with the pox virus vector, and the lentivirus proteins or portions thereof, self-assemble into defective, non-self-propagating lentivirus particles.

6. The pox virus vector of claim 5, wherein the pox virus is a vaccinia virus.

7. A pox virus vector having inserted therein, two DNA sequences from a single species of HIV, wherein one of the HIV DNA sequences is the env gene and the other of the HIV DNA sequences is selected from the group consisting of the gag gene and gag-pol gene, such that the HIV DNA sequences either express env and gag proteins, or express env and gag-pol proteins in a eukaryotic host cell infected with the pox virus vector, and the HIV proteins self-assemble into defective, non-self-propagating HIV particles.

8. A vaccinia virus vector comprising a first and a second chimeric gene inserted within the HindIII M Region of the vaccinia virus vector, wherein the first chimeric gene comprises an HIV env gene, or a portion thereof, operably linked to the vaccinia D1 promoter, the second chimeric gene comprises an HIV gag-pol gene, or a portion thereof, operable linked to the 40K vaccinia promoter, such that the gag, pol and env proteins, or portions thereof, are co-expressed in a eukaryotic host cell infected with the pox virus vector, and the gag, pol and env proteins, or portions thereof, self-assemble into defective, non-self-propagating HIV particles.

9. A vaccinia virus vector selected from the group consisting of vAbT408 and vAbT4674, such that HIV proteins are co-expressed in a eukaryotic host cell infected with the pox virus vector, and the HIV proteins self-assemble into defective, non-self-propagating HIV particles.

10. A self-assembled, defective, non-self-propagating lentivirus particle produced by a eukaryotic host infected with the pox virus vector of claim 5.

11. The lentivirus particle of claim 10, wherein the lentivirus is Human Immunodeficiency Virus (HIV).

12. A self-assembled, defective, non-self-propagating HIV particle produced by a eukaryotic host infected with the vaccinia virus vector of claim 8.

* * * * *